United States Patent [19]

Bartsch et al.

[11] Patent Number: 5,888,782
[45] Date of Patent: Mar. 30, 1999

[54] GENE AND GENE STRUCTURE CODING FOR AN AMINOTRANSFERASE, AND MICROORGANISMS WHICH EXPRESS THIS GENE

[75] Inventors: Klaus Bartsch, Steinbach; Arno Schulz, Hattersheim am Main; Eugen Uhlmann, Glashütten/Taunus, all of Germany

[73] Assignee: Hoechst Aktiengesellschaft, Frankfurt am Main, Germany

[21] Appl. No.: 337,453

[22] Filed: Nov. 4, 1994

Related U.S. Application Data

[60] Continuation of Ser. No. 974,470, Nov. 12, 1992, abandoned, which is a division of Ser. No. 450,230, Dec. 13, 1989, Pat. No. 5,221,737.

[30] Foreign Application Priority Data

Dec. 15, 1988 [DE] Germany .......................... 38 42 174.7
Sep. 26, 1989 [DE] Germany .......................... 39 32 015.4

[51] Int. Cl.$^6$ .............................. C12P 13/04; C12P 13/00; C12N 9/12; C12N 15/54
[52] U.S. Cl. ...................... 435/106; 435/128; 435/71.2; 435/172.3; 435/252.3; 435/320.1; 536/23.2
[58] Field of Search ..................................... 435/193, 106, 435/128, 71.2, 172.3, 252.3, 320.1; 536/23.2

[56] References Cited

U.S. PATENT DOCUMENTS

| | | | |
|---|---|---|---|
| 4,968,609 | 11/1990 | Ito et al. ................................. | 435/69.1 |
| 5,017,481 | 5/1991 | Matsui et al. ........................... | 435/108 |
| 5,120,654 | 6/1992 | Marquardt et al. ................. | 435/252.33 |
| 5,130,246 | 7/1992 | Schultz et al. .......................... | 435/193 |

FOREIGN PATENT DOCUMENTS

A-0248357 12/1987 European Pat. Off. .
A-0349965 1/1990 European Pat. Off. .

OTHER PUBLICATIONS

J. Geisselsoder et al., "Efficient Site–Directed *In Vitro* Mutgenesis", BioTechniques 5(8) :786–791 (1987).

H. Shiraishi et al., "A rapid and efficient method for targeted random mutagenesis", Gene 64:313–319 (1988).

Wilkinson et al., "A large increase in enzyme–substrate affinity by protein engineering", Nature 307:187–188. (1984).

Smith, "In Vitro Mutagenesis", Ann. Rev. Genet. 19:423–462 (1985).

Zoller and Smith, "Oligonucleotie–directed mutagenesis using M13–dereived vectors: an efficient and general procedure for the production of point mutations in any fragment of DNA, Nucleic Acids Research", 10(20) :6487–6500 (1982).

*Primary Examiner*—Rebecca E. Prouty
*Attorney, Agent, or Firm*—Finnegan, Henderson, Farabow, Garrett & Dunner, L.L.P.

[57] ABSTRACT

A gene and gene structure coding for an aminotransferase, and microorganisms which express this gene.

The preparation of L-2-amino-4-methylphosphinobutyric acid (L-PPT) by transamination of (3-carboxy-3-oxopropyl)-methylphosphinic acid with the aid of the L-PPT-specific transaminase from *E. coli* DH 1 is very much more efficient when the gene coding for this enzyme is isolated, incorporated into a plasmid and then a microorganism is transformed therewith.

5 Claims, 10 Drawing Sheets

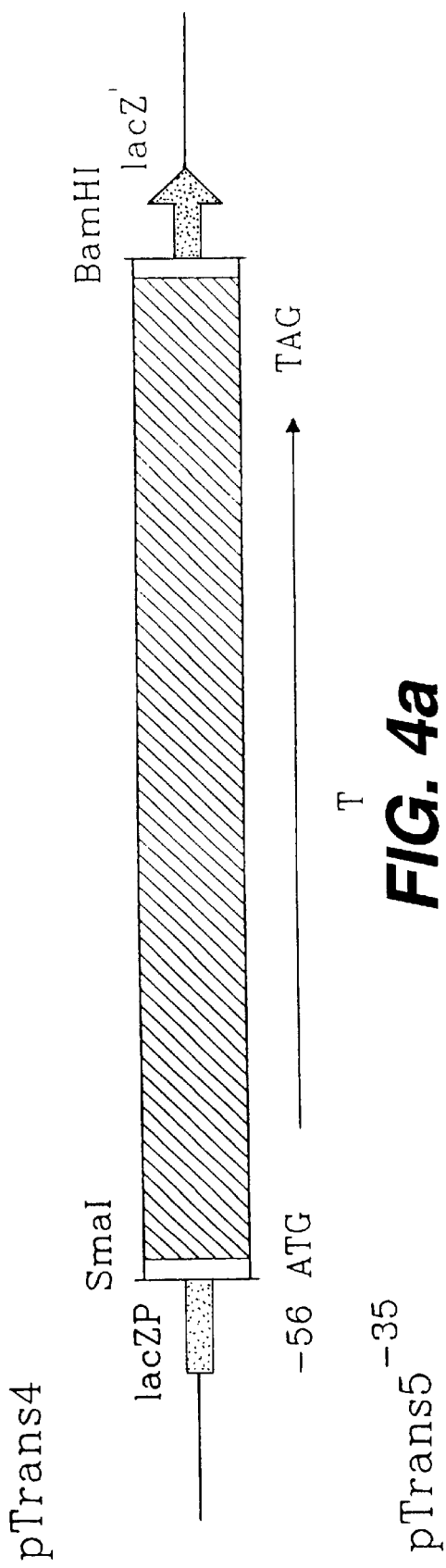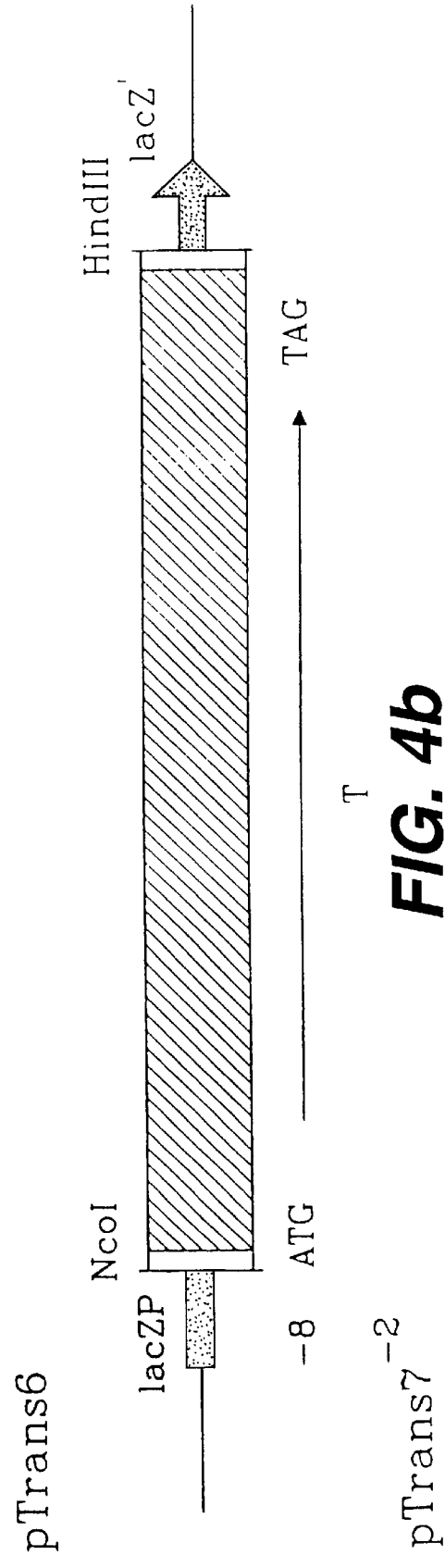

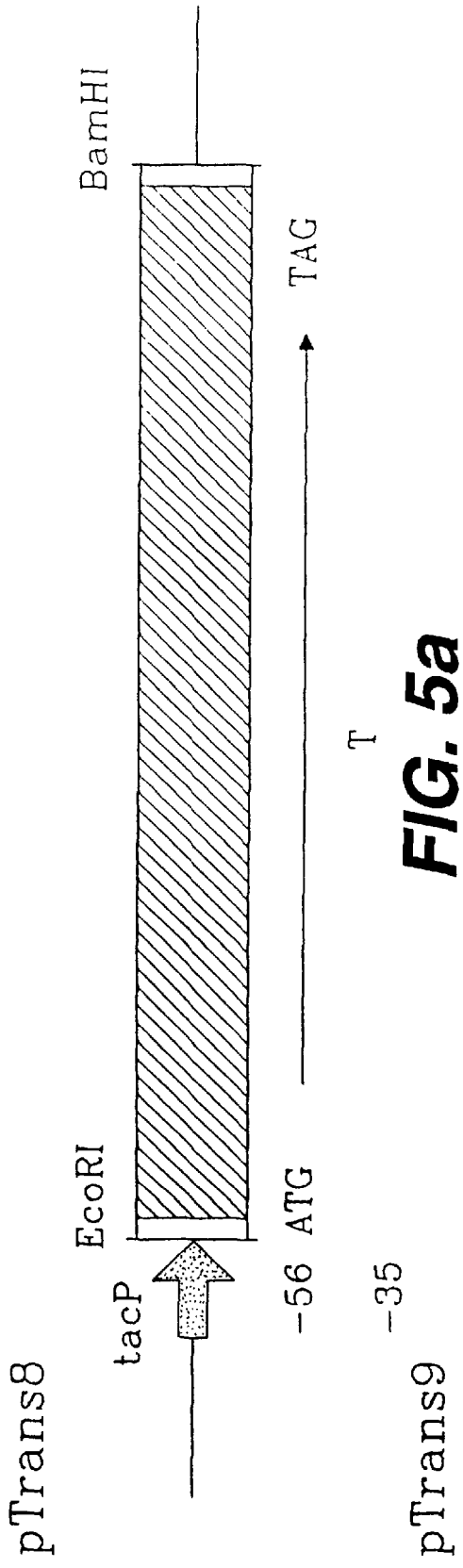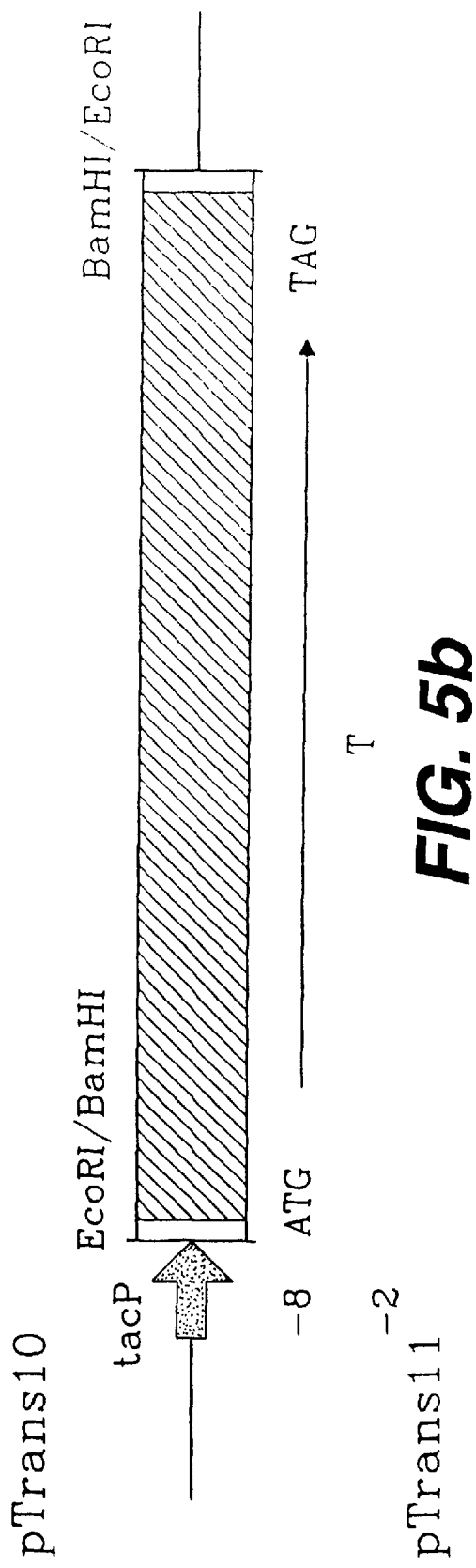

```
                                    289                    304                    319
ATG AAC AGC AAT AAA GAG TTA ATG CAG CGC AGT CAG GCG ATT
Met Asn Ser Asn Lys Glu Leu Met Gln Arg Ser Gln Ala Ile 334                    349                    364
CCC CGT GGC GTT GGG CAA ATT CAC CCG ATT TTC GCT GAC CGC GCG
Pro Arg Gly Val Gly Gln Ile His Pro Ile Phe Ala Asp Arg Ala 379                    394                    409
GAA AAC TGC CGG GTG GAC GTT GAA GGC CGT GAG TAT CTT GAT
Glu Asn Cys Arg Val Trp Asp Val Glu Gly Arg Glu Tyr Leu Asp 424                    439                    454
TTC GCG GGG GGG ATT GCG GTG CTC AAT ACC GGG CAC CTG CAT CCG
Phe Ala Gly Gly Ile Ala Val Leu Asn Thr Gly His Leu His Pro 469                    484                    499
AAG GTG GTG GCC GCG GTG GAA GCG CAG TTG AAA AAA CTG TCG CAC
Lys Val Val Ala Ala Val Glu Ala Gln Leu Lys Lys Leu Ser His 514                    529                    544
ACC TGC TTC CAG CTG GCT TAC GAG CCG TAT CTG GAG CTG TGC
Thr Cys Phe Gln Val Leu Ala Tyr Glu Pro Tyr Leu Glu Leu Cys 559                    574                    589
GAG ATT ATG AAT CAG AAG GTG CCG GGC GAT TTC GCC AAG AAA ACG
Glu Ile Met Asn Gln Lys Val Pro Gly Asp Phe Ala Lys Lys Thr
```

*FIG. 6a*

```
CTG CTG GTT ACG ACC GGT TCC GAA GCG GTG GAA AAC GCG GTA AAA
Leu Leu Val Thr Thr Gly Ser Glu Ala Val Glu Asn Ala Val Lys
                    604             619             634

ATC GCC CGC GCC ACC AAA CGT AGC GGC ACC GGC ATC GCT TTT AGC
Ile Ala Arg Ala Thr Lys Arg Ser Gly Thr Gly Ile Ala Phe Ser
                    649             664             679

GGC GCG TAT CAC GGG CGC ACG CAT TAC CTG ACG CTG GCG CTG ACC GGC
Gly Ala Tyr His Gly Arg Thr His Tyr Leu Thr Leu Ala Leu Thr Gly
                    694             709             724

AAG GTG AAT CCG TAC TCT GCG GGC ATG GGG CTG ATG CCG GGT CAT
Lys Val Asn Pro Tyr Ser Ala Gly Met Gly Leu Met Pro Gly His
                    739             754             769

GTT TAT CGC GCG CTT TAT CCT TGC CCG CTG CAC GGC ATA AGC GAG
Val Tyr Arg Ala Leu Tyr Pro Cys Pro Leu His Gly Ile Ser Glu
                    784             799             814

GAT GCT ATC GCC AGC ATC CAC CGG ATC TTC AAA AAT GAT GCC
Asp Ala Ile Ala Ser Ile His Arg Ile Phe Lys Asn Asp Ala
                    829             844             859

GCG CCG GAA GAT ATC GCC GCC ATC GTG ATT GAG CCG GTT CAG GGC
Ala Pro Glu Asp Ile Ala Ala Ile Val Ile Glu Pro Val Gln Gly
                    874             889             904
```

FIG. 6b

```
GAA GGC GGT TTC TAC GCC TCG TCG CCA TTT ATG CAG CGT TTA
Glu Gly Gly Phe Tyr Ala Ser Ser Pro Phe Met Gln Arg Leu
              919                   934                   949

CGC GCT CTG TGT GAC GAG CAC GGG ATC ATG CTG ATT GCC GAT GAA
Arg Ala Leu Cys Asp Glu His Gly Ile Met Leu Ile Ala Asp Glu
              964                   979                   994

GTG CAG AGC GGC GCG CGT ACC GGC ACG CTG TTT GCG ATG GAG
Val Gln Ser Gly Ala Arg Thr Gly Thr Leu Phe Ala Met Glu
              1009                  1024                  1039

CAG ATG GGC GTT GCG CCG GAT CTT ACC ACC TTT GCG AAA TCG ATC
Gln Met Gly Val Ala Pro Asp Leu Thr Thr Phe Ala Lys Ser Ile
              1054                  1069                  1084

GCG GGC GGC TTC CCG CTG GCC GGC GTC ACC GGG CGC GCG GAA GTA
Ala Gly Gly Phe Pro Leu Ala Gly Val Thr Gly Arg Ala Glu Val
              1099                  1114                  1129

ATG GAT GCC GCT CCA GGC GGT CTG GGC ACC TAT GCG GGT
Met Asp Ala Val Ala Pro Gly Gly Leu Gly Thr Tyr Ala Gly
              1144                  1159                  1174

AAC CCG ATT GCC TGC GTG GCT GCG CTG GAA GTG TTG AAG GTG TTT
Asn Pro Ile Ala Cys Val Ala Ala Leu Glu Val Leu Lys Val Phe
              1189                  1204                  1219
```

FIG. 6c

```
                                1249                      1264
GAG CAG GAA AAT CTG CTG CAA AAA GCC AAC GAT CTG GGG CAG AAG
Glu Gln Glu Asn Leu Leu Gln Lys Ala Asn Asp Leu Gly Gln Lys 1294                      1309
TTG AAA GAC GGA TTG CTG GCG ATA GCC GAA AAA CAC CCG GAG ATC
Leu Lys Asp Gly Leu Leu Ala Ile Ala Glu Lys His Pro Glu Ile 1339                      1354
GGC GAC GTA CGC GGG CTG GGG GCG ATG ATC GCC ATT GAG CTG TTT
Gly Asp Val Arg Gly Leu Gly Ala Met Ile Ala Ile Glu Leu Phe 1384                      1399
GAA GAC GGC GAT CAC AAC AAG CCG GAC GCC AAA CTC ACC GCC GAG
Glu Asp Gly Asp His Asn Lys Pro Asp Ala Lys Leu Thr Ala Glu 1429                      1444
ATC GTG GCT CGC GCC CGC GAT AAA GGC CTG ATT CTT CTC TCC TGC
Ile Val Ala Arg Ala Arg Asp Lys Gly Leu Ile Leu Leu Ser Cys 1474                      1489
GGC CCG TAT TAC AAC GTG CTT GTA CCG CTC ACC ATT
Gly Pro Tyr Tyr Asn Val Leu Val Pro Leu Thr Ile 1519                      1534
GAA GAC GCT CAG ATC CGT CAG GGT CTG GAG ATC ATC AGC CAG TGT
Glu Asp Ala Gln Ile Arg Gln Gly Leu Glu Ile Ile Ser Gln Cys
```

FIG. 6d

```
                          1549
TTT GAT GAG GCG AAG CAG TAG
Phe Asp Glu Ala Lys Gln ***
```

*FIG. 6e*

GENE AND GENE STRUCTURE CODING FOR AN AMINOTRANSFERASE, AND MICROORGANISMS WHICH EXPRESS THIS GENE

This application is a continuation of application Ser. No. 07/974,470, filed Nov. 12, 1992, now abandoned, which is a divisional application of Ser. No. 07/450,230, filed Dec. 13, 1989 now U.S. Pat. No. 5,221,737.

CROSS-REFERENCE TO RELATED APPLICATION

U.S. patent application Ser. No. 07/359,591, filed Jun. 1, 1989, corresponds to (and claims priority of) German Patent Application P 38 18 851.1 (to be published on or about Dec. 7, 1989, as German Offenlegungsschrift DE 3,818,851 A1) and European Patent Application EP-A2 0,344,683, to be published on Dec. 6, 1989.

German Offenlegungsschrift 38 18 851 (which has not been prior-published and corresponds to EP-A2 0 344 683 published on Dec. 6, 1989) has already proposed an aminotransferase (transaminase) which was isolated from *E. coli* DH-1.

The gene which codes for this new transaminase has now been found. It is possible thereby, according to the invention, to prepare the enzyme in larger amounts than in accordance with the earlier proposal, but also to carry out the specific transamination reactions with a microorganism transformed according to the invention. Thus, the isolation and characterization of the gene permits very much more efficient transaminations than are possible with the enzyme isolated according to the earlier proposal.

German Offenlegungsschrift 38 18 851 characterizes the new enzyme, inter alia, by the amino acid sequence of the N terminus. The first 30 of these amino acids are shown below:

```
            1              5             10                  15
NH2—MET ASN SER ASN LYS GLU LEU MET GLN ARG ARG SER GLN ALA ILE
           16             20             25                  30
    PRO ARG GLY VAL GLY GLN ILE HIS PRO ILE PHE ALA ASP ARG ALA --
```

In the region of amino acids 4 to 10 there are methionine, which is coded for by only one triplet, as well as four amino acids which are encoded by only two triplets. Only leucine is six-fold "degenerate" in the genetic code. This sequence is thus particularly well suited for the construction of a probe of 20 nucleotides (20mer):

```
5 -AAC AAA GAA TTA ATG CAA CG-3
     T   G   G C G         G A
                 C
                 T
```

This probe was synthesized by the phosphoramidite method in a manner known per se. Additionally synthesized was a 38mer of the non-coding strand for amino acids 15 to 27.

This oligonucleotide was also synthesized by the phosphoramidite method.

These probes were employed to screen a cosmid gene bank of *E. coli* DH 1. Hybridization-positive clones were initially assayed for elevated L-PPT transaminase activity and then characterized in detail by restriction mapping. It was possible by subcloning and activity assays of subfragments to localize the position of the gene in the genome and subsequently to define it even further by exonuclease degradation. Thus, initially a 15 kb SalI fragment on which the gene according to the invention is located was identified, as was a 3.8 kb SalI/BamHI fragment which allowed the orientation of the gene to be established (FIG. 1). The latter fragment also contains the gene's own promoter. It was thus possible, merely by cloning restriction fragments into suitable vectors, to increase the transaminase activity by about fifty times compared with the starting strain.

The yield of enzyme or enzyme activity can also be influenced by choosing suitable culture conditions. Thus, for example, the glucose content in the medium plays a considerable role, depending on the choice of the expression system: at concentrations above 0.05% there may be a drastic fall in the enzyme activity. This dependence is evident even with control strains which express only the copy of the transaminase gene in the bacterial chromosome.

In a further development of this concept of the invention it was then possible to localize the gene coding for the aminotransferase more accurately: the gene is located on a 1.6 kb DraI/BamHI fragment (FIG. 2) which contains an open reading frame which is 1281 nucleotides long (including the stop codon) and codes for a protein of 426 amino acids.

The DNA sequence is depicted in Table 1. The ATG start codon starts with nucleotide no. 275, and the TAG stop codon starts with nucleotide no. 1553.

FIG. 6 shows the coding strand of the gene as well as the amino acid sequence of the transaminase according to the invention. The latter shows only a few homologies of sequence with the other known transaminases from *E. coli* (aspC, tyrB, hisC, ilvE, avtA and serC).

Because of the substrate specificity of the L-PPT transaminase for 4-aminobutyric acid (GABA) and comparison of the restriction map of the 15 kb SalI fragment (see FIG. 1) with the physical map of the *E. coli* K-12 genome [Kohara et al. (1987), Cell 50: 495–508], it was possible to identify the cloned transaminase gene as gabT, a locus from the *E. coli* K-12 gab cluster at 57.5 min [Metzer et al. (1979), J. Bacteriol. 137; 1111–1118].

Knowledge of the gene allows the structural gene to be provided with strong promoters in a directed manner. The gene constructs obtained in this way not only show higher expression rates than the previously mentioned expression plasmids but also permit their activity to be controlled by inducers. It is furthermore possible to choose expression

```
3-TAG GGC GCG CCG CAA CCG GTC TAG GTG GGC TAG AAG CG-5
     T           T       T           T
``` systems which exhibit no catabolite repression, such as the tac system, so that bacteria transformed with such gene constructs can also be fermented in the presence of glucose in the nutrient medium. This makes high cell densities possible and thus achieves high yields relative to the fermenter volume.

BRIEF DESCRIPTION OF THE FIGURES

FIG. 4 shows the location of the gene according to the invention in the vectors pTrans4 to pTrans7.

FIG. 5 shows the location of the gene according to the invention in the vectors pTrans8 to pTrans11.

FIG. 6 shows the DNA sequence and amino acid sequence of the gene for a transaminase specific for L-2-amino-4-methylphosphinobutyric acid (L-PPT).

Hence the invention relates to a gene for a transaminase specific for L-2-amino-4-methylphosphinobutyric acid (L-PPT), located on a 1.6 kb DraI/BamHI fragment from the genome of E. coli DH 1, having the DNA sequence shown in FIG. 6, and, furthermore, to a gene coding for an enzyme having the amino acid sequence shown in FIG. 6 as well as for enzymes which have the same action and whose amino acid sequence is derived from that shown in FIG. 6 by addition, deletion or exchange of amino acids.

The invention additionally relates to a transaminase specific for L-2-amino-4-methylphosphinobutyric acid (L-PPT) and has an amino acid sequence which is derived from that shown in FIG. 6 by addition, deletion or exchange of amino acids.

The invention furthermore relates to plasmids containing a gene of this type, and to microorganisms, in particular *E. coli*, containing a plasmid of this type.

The invention also relates to a process for the stereoselective production of L-PPT from (3-carboxy-3-oxopropyl)-methylphosphinic acid by transamination with microorganisms, which comprises employing a microorganism which is transformed with one of the plasmids specified above, or wherein an enzyme which is modified (as above) by modification of the amino acid sequence is employed.

The invention is explained in detail in the examples which follow. Percentage data in these relate to weight.

EXAMPLE 1

Cloning of the L-PPT transaminase gene from *E. coli* DH 1/construction of expression plasmids Chromosomal DNA from *E. coli* DH 1 was isolated by the method described in Ausubel et al. (1987), Current Protocols in Molecular Biology: 5.3.2.–5.4.3., 5.7.1.–5.7.3., partially cleaved with Sau3A and fractionated by size in an agarose gel. DNA fragments about 25–40 kb in size were ligated into the cosmid vector pTBE [Grosveld, F. G. et al. (1982), Nucleic Acids Research 10: 6715] which had been cut with BamHI and were packaged into lambda phages [Amersham: in vitro packaging system for Lambda DNA, Code No. 334Z, and Maniatis et al. (1982), Molecular Cloning, A Laboratory Manual, Cold Spring Harbor: 296–299]. Transfection of the recipient strain *E. coli* DH 1 was followed by isolation of 2000 single clones, which corresponds to several genome-equivalents of *E. coli*. Two oligonucleotides corresponding to regions of the N-terminal amino acid sequence of the L-PPT transaminase protein (20mer and 38mer, see text) were synthesized in order to find the gene which was sought in the cosmid gene bank which had been constructed.

Figure 1:
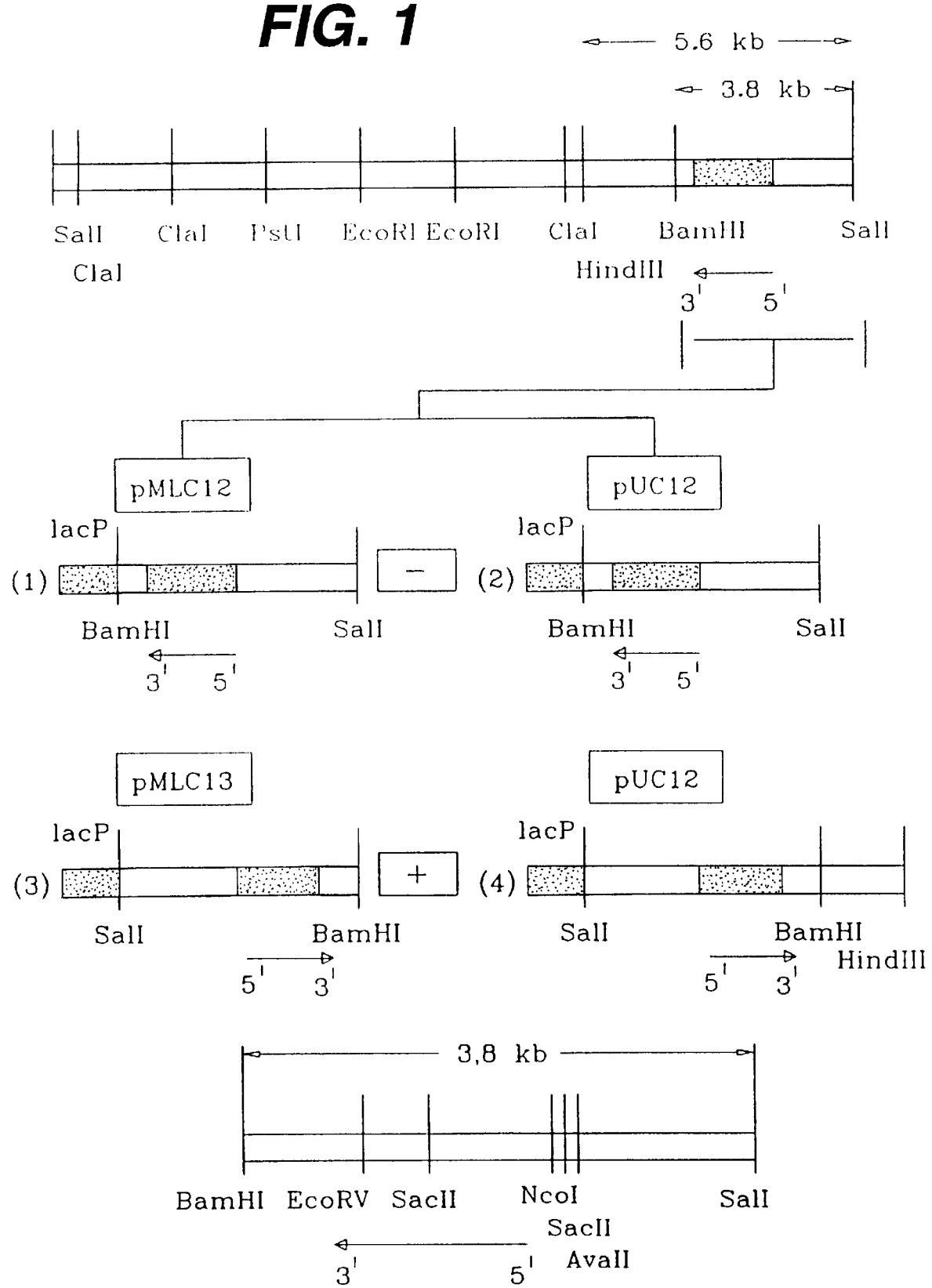
FIG. 1 shows the localization of the gene according to the invention onto a DNA fragment 3.8 kb in size.

Subsequently the cosmids isolated from the single clones were bound (in accordance with Maniatis et al.: 331) to nitrocellulose filters (Schleicher and Schüll BA85) with the aid of a BRL Dot-Blot suction apparatus and were hybridized with the 32P-end-labeled oligonucleotides (Ausubel et al.: 6.4.1.–6.4.4.). 2 of 4 hybridization-positive clones showed a 3- to 5-fold increase in activity in the L-PPT transaminase enzyme assay (see below, Example 2). The two clones contained an identical 15 kb SalI insertion whose restriction map is depicted in FIG. 1.

A 5.6 kb HindIII/SalI fragment and a 3.8 kb BamHI/SalI fragment from this DNA segment, both of which hybridized with the 5'-specific oligonucleotides of L-PPT transaminase, were cloned in both orientations behind the *E. coli* lac promoter into the vectors pUC12 and pMLC12/13 [Perbal, B. (1984), A Practical Guide to Molecular Cloning: 259–272], and the recombinant plasmids were subsequently assayed for transaminase activity (FIG. 1). Whereas the enzyme activities of the constructs (1) and (2) were only a little above the background, the L-PPT transaminase expression shown by (3) and (4) (pTrans2 and pTrans3, FIG. 3), which contained the same DNA fragment in the opposite orientation to the lac promoter, conferred to (1) and (2), was increased about 50-fold. It was possible to establish from this the direction of transcription of the gene, as depicted in FIG. 1.

The location of the transaminase gene on the 3.8 kb BamHI/SalI fragment was established more accurately by further restriction mapping as well as by preparing a series of ExoIII/S1 deletions [Henikoff, S. (1984), Gene 28: 351–359]. In the latter method the 3.8 kb fragment cloned into pMLC12/13 was subjected to enzymatic digestion, in each case starting from one end, for various lengths of time. The truncated insertions were subsequently assayed for enzymatic activity. On the assumption that parts of the transaminase structural gene had been deleted in DNA fragments which no longer had activity, it was possible to establish the location of the gene, as shown in FIG. 1 below.

Figures 3A, 3B, 3C:
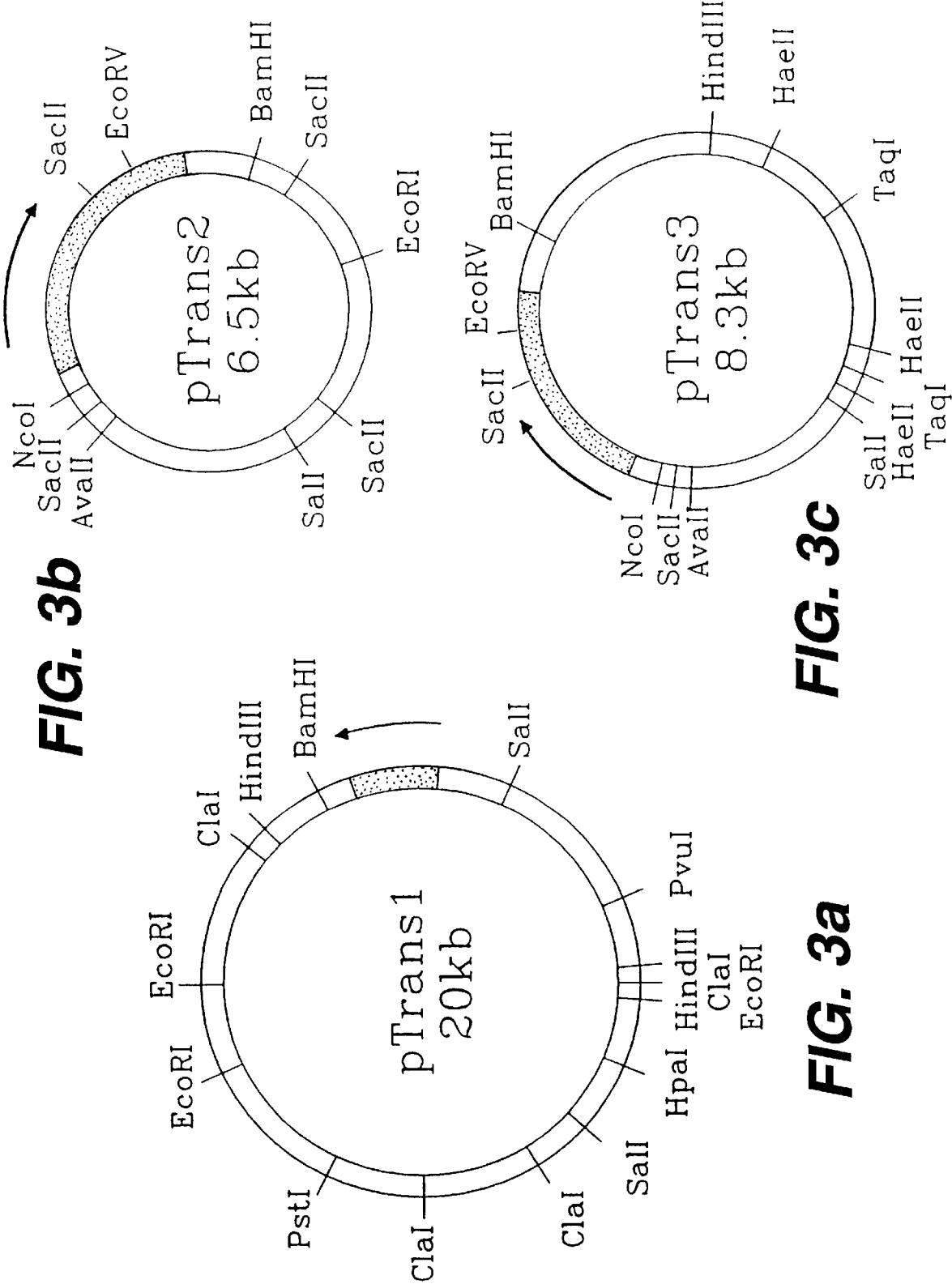
FIG. 3 shows the initially developed vectors pTrans1, pTrans2 and pTrans3.

FIG. 3 depicts three different recombinant plasmids which carry the cloned L-PPT transaminase gene from *E. coli* DH 1 and are used in the Examples which follow. The plasmid pTrans1 contains the 15 kb SalI insert in the cosmid vector pTBE and expresses the transaminase under the control of the endogenous promoter. The two other constructs are expression plasmids with the *E. coli* lac promoter: pTrans2 contains the 3.8 kb BamHI/SalI fragment in pMLC13, pTrans3 contains the 5.6 kb HindIII/SalI fragment in pUC12.

EXAMPLE 2

L-PPT production in *E. coli* DH 1 with various transaminase expression plasmids

*E. coli* DH 1 transformants with the recombinant plasmids pTrans1, pTrans2 and pTrans3 and with the vector plasmids pTBE, pMLC13 and pUC12 as control were cultured in 10 ml cultures in LB medium [Luria-Bertani Medium, Maniatis et al. (1982): 68] with 50 μg of the appropriate antibiotic (ampicillin in the case of pTrans1, pTrans3, pTBE and pUC12, and chloramphenicol in the case of pTrans2 and pMLC13) at 37° C. for 15 h. The cells were then removed by centrifugation at 5000×g for 5 min, washed twice in 5 ml each time of 10 mM NaCl, 10 mM sodium phosphate (pH=7.5) and resuspended for the transaminase activity assay in 1 ml of reaction mix (5 mM NaCl, 5 mM sodium phosphate, 30 g/l (3-carboxy-3-oxopropyl)-methylphosphinic acid, 90 g/l L-glutaminic acid, 100 mM Tris/HCl, pH=8.0). The cells were incubated in this solution while shaking at 37° C. for 1 h and then denatured at 95° C. for 10 min. The reaction supernatants were analyzed for L-PPT production in an amino acid analyzer (Biotronic Amino Acid Analyzer LC 5001, 3.2×130 mm BTC-2710 column).

The space-time yields achieved with the various constructs are compiled in Tab. 2. By far the highest enzyme activities were achieved with the two lac expression plasmids, with the result for the pUC12 derivative pTrans3 being even better, presumably because of the larger copy number per cell, than for the pMLC13 derivative pTrans2. The space-time yields measured for pTrans3 were about 60 times higher than the results for the control cells transformed with pUC12 vector plasmid.

TABLE 2

L-PPT production in *E. coli* DH 1 with various transaminase expression plasmids

| Plasmid: | Space-time yield (mg of L-PPT produced/l/h): |
|---|---|
| pTBE | 100 |
| pMLC13 | 60 |
| pUC12 | 70 |
| pTrans1 | 300 |
| pTrans2 | 2400 |
| pTrans3 | 4300 |

EXAMPLE 3

Effect of the glucose concentration in the culture medium on the L-PPT transaminase activity

*E. coli* DH 1-pTrans3 and *E. coli* DH 1-pUC12 were cultured in 10 ml of LB medium without glucose and with increasing glucose concentrations (0.01%, 0.05%, 0.1% and 0.5%), worked up and assayed for L-PPT transaminase activity as in Example 2. The result is shown in Tab. 4. Both the lac-expressed transaminase gene on the plasmid pTrans3 and the chromosomal gene from the control strain (with pUC12) were repressed by glucose concentrations >0.05%. The maximum rate of L-PPT synthesis was achieved with 0.05% glucose in the medium.

TABLE 3

Dependence of the L-PPT transaminase activity in *E. coli* DH-1 on the glucose concentration in the culture medium

| Glucose concentration in the medium (%) | Rel. transaminase activity (%) | |
|---|---|---|
| | pUC12 | pTrans3 |
| 0 | 8 | 100[a] |
| 0.01 | 18 | 184 |
| 0.05 | 22 | 276 |
| 0.1 | 12 | 18 |
| 0.5 | 2 | 8 |

[a]The activity of pTrans3 without glucose was set equal to 100%.

EXAMPLE 4

Overexpression of L-PPT transaminase protein from *E. coli* DH 1

*E. coli* DH 1-pTrans3 and *E. coli* DH 1-pUC12 were cultured as in Example 3. The cells were washed and resuspended in 1 ml of 10 mM NaCl, 10 mM sodium phosphate (pH=7.5) and then disrupted by sonication for 5×20 sec, and aliquots of these crude extracts, with equal amounts of protein, were applied to a 12.5% SDS/polyacrylamide gel [Laemmli, U.K. (1970), Nature 227: 680].

The overexpressed L-PPT transaminase protein appears in the protein pattern of extracts from *E. coli* DH 1-pTrans3 as an additional band of 43,000 Dalton. This is absent in the expression strain in the sample with 0.5% glucose in the culture medium as well as in the control strain *E. coli* DH 1-pUC12 with 0.05% glucose.

EXAMPLE 5

Sequencing of the L-PPT transaminase gene from *E. coli* K 12

Figure 2:
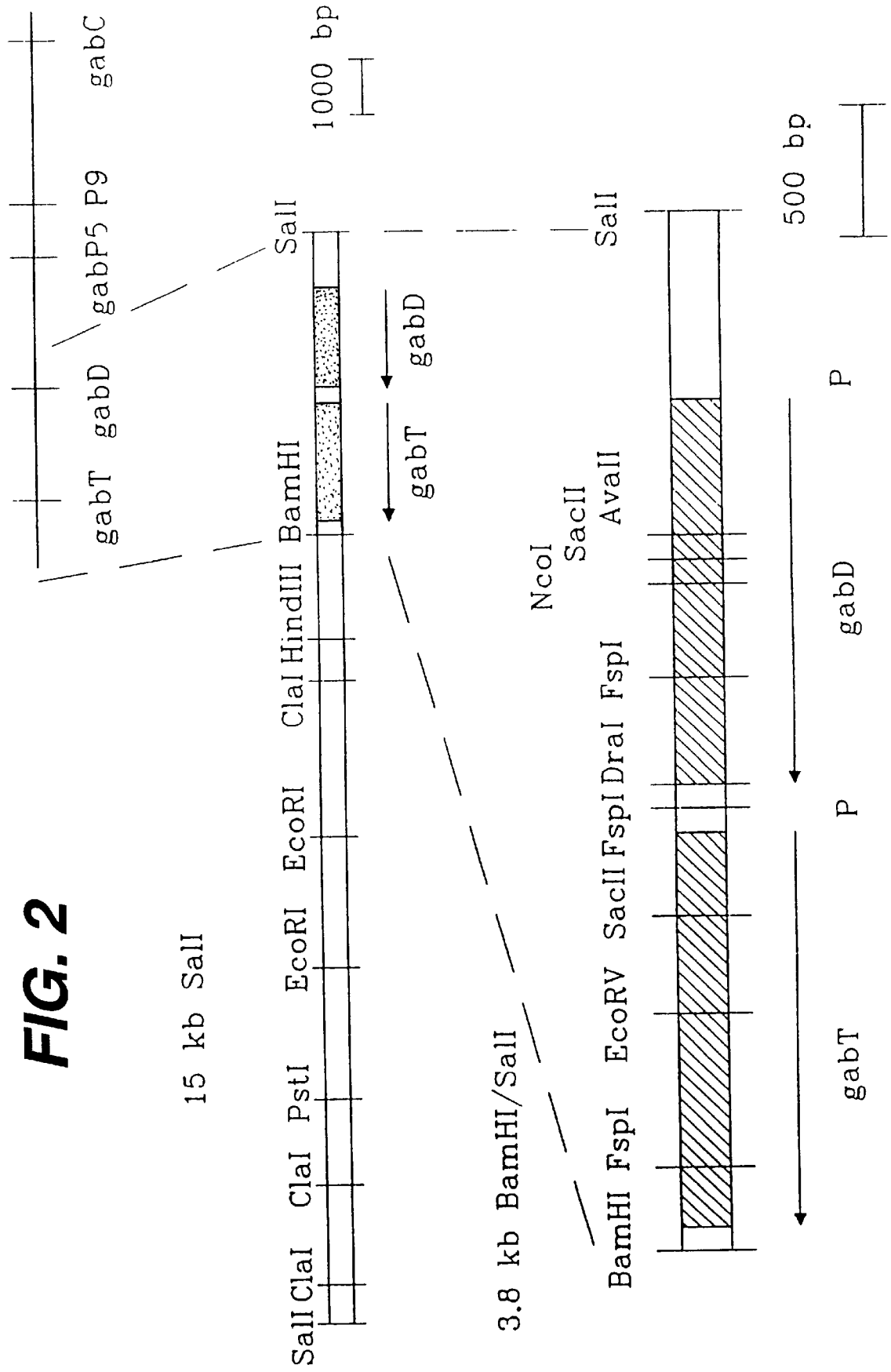
FIG. 2 demonstrates that this fragment contains another gene (gab D) besides the desired gene (gab T).

It was possible, by further subcloning and activity assays of restriction fragments of the 3.8 kb BamHI/SalI fragment, to localize the L-PPT transaminase gene to a 1.6 kb DraI/BamHI DNA fragment (FIG. 2). The latter was sequenced by the dideoxy method [Sanger, F. et al. (1977), Proc. Natl. Acad. Sci. USA 74: 5463–5468] with α-[35S]-dATP and double-stranded DNA as templates [Chen, E. Y. and Seeburg, P. H. (1985), DNA 4: 165–170]. For this purpose, deletions prepared by ExoIII/S1 nuclease digestion and starting from the 3' end (BamHI cleavage site) of the gene [Henikoff, S. (1984), Gene 28: 351–359], as well as a number of restriction fragments of the 1.6 kb DraI/BamHI fragment, were cloned in a known manner [Maniatis et al. (1982), Molecular Cloning, A Laboratory Manual, Cold Spring Harbor] into the vectors pMLC12/13 and pUC12/13 and sequenced with commercially available primers (from the pUC sequencing kit, Boehringer Mannheim, Order No. 1013 106). In addition, synthetic oligonucleotides which it was possible to prepare (phosphoramidite method) on the basis of sequence information already available were also used as sequencing primers. The exact restriction map of the 1.6 kb DraI/BamHI fragment is shown in FIG. 2.

EXAMPLE 6

Preparation of expression plasmids with the L-PPT transaminase structural gene from *E. coli* K-12 a) lac expression plasmids

In order to fuse the transaminase structural gene with another promoter, it was necessary to delete as far as possible the non-coding 5' region of the 1.6 kb DraI/BamHI fragment above the ATG start codon. For this purpose, the DNA fragment was truncated from the DraI end using the ExoIII/S1 nuclease technique described above. Two of the deletions prepared in this way [−56 to ATG and −35 to ATG, see Table 4, constructs (I) and (II)] were cloned as SmaI/BamHI fragments behind the lac promoter in the vector pUC12 cut with SmaI/BamHI. The expression plasmids pTrans4 and pTrans5 obtained in this way are depicted in FIG. 4.

In another approach, an NcoI cleavage site was introduced into the transaminase gene in the region of the ATG start codon or in the position −6 by in vitro mutagenesis using the Tag polymerase chain reaction (PCR) technique [Higuchi et al. (1988), Nucleic Acids Research 16: 7351–7367] [see Table 4, constructs (III) and (IV)]. Whereas the NcoI cleavage site in position −6 does not affect the transaminase structural gene, the mutation in the region of the start codon alters amino acid 2 of the transaminase from Asn to Asp. However, this conservative amino acid replacement has no effect on the activity of the enzyme protein. It was now possible, because of the restriction cleavage sites introduced into the two constructs (III) and (IV), to clone the transaminase structural gene without 5'-non coding sequences, in each case as NcoI/HindIII fragment, behind the lac promoter into the vector pMG12 (pUC12 derivative with modified polylinker: EcoRI-SmaI-BamHI-NcoI-NheI-HgiAI-PstI-KpnI-XbaI-ClaI-SalI-SacII-SphI-PvuI-HindIII), cut with NcoI/HindIII (FIG. 4: plasmids pTrans6 and pTrans7). In order to examine the expression of transaminase with the various gene constructs, E. coli JM103 transformants with the recombinant plasmids pTrans4, pTrans5, pTrans6, pTrans7, as well as pTrans3 (see Example 1) and the vector plasmid pUC12 as control, were cultured in 10 ml of LB medium without and with glucose (0.5%). The L-PPT-specific transaminase activities were measured as described in Example 2 and reported in nmol of L-PPT/min/mg of cells. The results are compiled in Table 5. The enzyme activities with these lac expression plasmids are a factor of approximately 2 higher than with the plasmid pTrans3. All the constructs show catabolite repression in the presence of glucose.

b) tac expression plasmids

The expression vector pJF118u was used for the expression of the L-PPT transaminase gene with the hybrid tac promoter (lac and trp portions). It is a derivative of pKK223-3 and contains, immediately behind the tac promoter sequence, a polylinker with the restriction cleavage sites EcoRI-SmaI-BamHI-SalI-PstI-HindIII. In addition, the vector expresses the lacI gene coding for the lac repressor, so that the activity of the tac promoter can be induced by IPTG. The tac promoter is not subject to catabolite repression by glucose. The transaminase gene constructs (I) and (II) (ExoIII/S1 nuclease deletions, −56 and −35, respectively, to ATG), which are depicted in Table 4, were cloned as EcoRI/BamHI fragments behind the tac promoter in the vector pJF118u cut with EcoRI/BamHI. FIG. 5 shows the recombinant plasmids pTrans8 and pTrans9 obtained in this way. The transaminase gene constructs (III) and (IV) prepared by in vitro mutagenesis (see Table 4) were isolated as BamHI fragments from the plasmids pTrans6 and pTrans7, and the cohesive ends were filled in with Klenow enzyme. These fragments were cloned behind the tac promoter in pJF118u cut with EcoRI and treated with S1 nuclease. The only isolated subclones which were used further were those which contained the L-PPT transaminase structural gene in the correct orientation to the tac promoter (see FIG. 5, recombinant plasmids pTrans10 and pTrans11). To determine the L-PPT-specific transaminase activities, E. coli JM103 transformants with the recombinant plasmids pTrans8, pTrans9, pTrans10, pTrans11, as well as pTrans3 and the vector plasmid pJF118u as control, were cultured in 10 ml of LB medium without and with glucose (0.5%) and harvested after 8 h. In parallel mixtures, after an O.D.$5_{600\,nm}$ of 0.5 had been reached, the cells were induced with 1 mM IPTG for 4 h and then likewise harvested. The transaminase activities were determined as described in 6. a). The results of the enzyme measurements are compiled in Table 6. All four tac expression plasmids are, by comparison with the plasmid pTrans3, inducible by IPTG and show no catabolite repression in the presence of glucose. The highest enzyme activities in the glucose medium were achieved with the plasmid pTrans11 and are comparable with the values reached with the lac expression constructs in glucose-free medium.

EXAMPLE 7

Production of L-PPT transaminase by fermentation

For the fermentation, the transaminase expression plasmid pTrans7 was transformed into the producer strain E. coli W3110 [Campbell et al. (1978), Proc. Natl. Acad. Sci. USA 75: 2276–2280]. The cells were inoculated into fermentation medium [M9 mineral medium described by Maniatis et al. (1982), Molecular Cloning, A Laboratory Manual, Cold Spring Harbor: 68–69, with 4% maltose as carbon source, 2% casamino acids and 0.4% GABA] and cultivated in a 10 l fermenter (Biostat 5, Braun Melsungen) at a constant stirrer speed (400 rpm), aeration (2 $m^3$/h) and automatic pH control (pH=7.0) and at 35° C. for 24 h. The optical density of the culture, as well as the L-PPT-specific transaminase activity of the cells, were measured during the fermentation by removing control samples. The bacteria were harvested after 24 h at a specific transaminase activity of 0.35 nkat/mg of cells (1 nkat=1 nmol of L-PPT/sec) and an optical density of 29 (corresponding to a mass of 3 kg wet weight of cells) and subsequently concentrated ten-fold using a cell separator (Westfalia model SA1-02-575). After addition of 20 mM sodium phosphate, pH=7.0, 0.01 mM pyridoxal phosphate, 5 mM 2-mercaptoethanol and 1 mM phenylmethanesulfonyl fluoride (PMSF), the bacteria were disrupted in a microfluidizer (model M-110 TIV, Micro Fluids, Newton USA) under 800 bar. The crude extract was incubated at 70° C. for 10 min, and the cell detritus plus the precipitated proteins were subsequently removed by centrifugation at 6000×g for 20 min. The supernatant after this treatment contained 16 g of protein with an L-PPT-specific transaminase activity of 7480 nkat/mg of protein. The transaminase activity measured in supernatants, prepared in the same way, of the untransformed producer strain W3110 was only 200 nkat/mg of protein, which corresponds to an approximately 40-fold increase in the enzyme activity by the recombinant plasmid pTrans7. SDS gel analysis of the proteins [Laemmli, U.K. (1970), Nature 227: 680] shows that the L-PPT transaminase is distinctly the predominant protein in the worked-up fermentation supernatants after the thermal precipitation at 70° C. This degree of enrichment of the transaminase is sufficient for the material to be used directly for immobilization of the enzyme on a carrier by the method proposed in German Offenlegungsschrift 3,818,851.

TABLE 1

```
DraI                    FspI
TTTAAAGATGAAGCTGATGTGATTGCGCAAGCCAATGACACCGAGTTTGGCCTTGCCGCCTATTTCTACGCC
AAATTTCTACTTCGACTACACTAACGCGTTCGGTTACTGTGGCTCAAACCGGAACGGCGGATAAAGATGCGG
         12          24          36          48          60          72

--------------------------------------------------------------------------------

CGTGATTTAAGCCGCGTCTTCCGCGTGGGCGAAGCGCTGGAGTACGGCATCGTCGGCATCAATACCGGCATT
GCACTAAATTCGGCGCAGAAGGCGCACCCGCTTCGCGACCTCATGCCGTAGCAGCCGTAGTTATGGCCGTAA
         84          96         108         120         132         144

--------------------------------------------------------------------------------
```

TABLE 1-continued

```
ATTTCCAATGAAGTGGCCCCGTTCGGCGGCATCAAAGCCTCGGGTCTGGGTCGTGAAGGTTCGAAGTATGGC
TAAAGGTTACTTCACCGGGGCAAGCCGCCGTAGTTTCGGAGCCCAGACCCAGCACTTCCAAGCTTCATACCG
         156           168           180           192           204           216

ATCGAAGATTACTTAGAAATCAAATATATGTGCATCGGTCTTTAACTGGAGAATGCGAATGAACAGCAATAA
TAGCTTCTAATGAATCTTTAGTTTATATACACGTAGCCAGAAATTGACCTCTTACGCTTACTTGTCGTTATT
         228           240           252           264           276           288

AGAGTTAATGCAGCGCCGCAGTCAGGCGATTCCCCGTGGCGTTGGGCAAATTCACCCGATTTTCGCTGACCG
TCTCAATTACGTCGCGGCGTCAGTCCGCTAAGGGGCACCGCAACCCGTTTAAGTGGGCTAAAAGCGACTGGC
         300           312           324           336           348           360

CGCGGAAAACTGCCGGGTGTGGGACGTTGAAGGCCGTGAGTATCTTGATTTCGCGGGCGGGATTGCGGTGCT
GCGCCTTTTGACGGCCCACACCCTGCAAGTTCCGGCACTCATAGAACTAAAGCGCCCGCCCTAACGCCACGA
         372           384           396           408           420           432

SacII
CAATACCGGGCACCTGCATCCGAAGGTGGTGGCCGCGGTGGAAGCGCAGTTGAAAAAACTGTCGCACACCTG
GTTATGGCCCGTGGACGTAGGCTTCCACCACCGGCGCCACCTTCGCGTCAACTTTTTTGACAGCGTGTGGAC
         444           456           468           480           492           504

CTTCCAGGTGCTGGCTTACGAGCCGTATCTGGAGCTGTGCGAGATTATGAATCAGAAGGTGCCGGGCGATTT
GAAGGTCCACGACCGAATGCTCGGCATAGACCTCGACACGCTCTAATACTTAGTCTTCCACGGCCCGCTAAA
         516           528           540           552           564           576

CGCCAAGAAAACGCTGCTGGTTACGACCGGTTCCGAAGCGGTGGAAAACGCGGTAAAAATCGCCCGCGCCGC
GCGGTTCTTTTGCGACGACCAATGCTGGCCAAGGCTTCGCCACCTTTTGCGCCATTTTTAGCGGGCGCGGCG
         588           600           612           624           636           648

CACCAAACGTAGCGGCACCATCGCTTTTAGCGGCGCGTATCACGGGCGCACGCATTACACGCTGGCGCTGAC
GTGGTTTGCATCGCCGTGGTAGCGAAAATCGCCGCGCATAGTGCCCGCGTGCGTAATGTGCGACCGCGACTG
         660           672           684           696           708           720

BssHII
CGGCAAGGTGAATCCGTACTCTGCGGGCATGGGGCTGATGCCGGGTCATGTTTATCGCGCGCTTTATCCTTG
GCCGTTCCACTTAGGCATGAGACGCCCGTACCCCGACTACGGCCCAGTACAAATAGCGCGCGAAATAGGAAC
         732           744           756           768           780           792

CCCGCTGCACGGCATAAGCGAGGATGACGCTATCGCCAGCATCCACCGGATCTTCAAAAATGATGCCGCGCC
GGGCGACGTGCCGTATTCGCTCCTACTGCGATAGCGGTCGTAGGTGGCCTAGAAGTTTTTACTACGGCGCGG
         804           816           828           840           852           864

EcoRV
GGAAGATATCGCCGCCATCGTGATTGAGCCGGTTCAGGGCGAAGGCGGTTTCTACGCCTCGTCGCCAGCCTT
CCTTCTATAGCGGCGGTAGCACTAACTCGGCCAAGTCCCGCTTCCGCCAAAGATGCGGAGCAGCGGTCGGAA
         876           888           900           912           924           936

TATGCAGCGTTTACGCGCTCTGTGTGACGAGCACGGGATCATGCTGATTGCCGATGAAGTGCAGAGCGGCGC
ATACGTCGCAAATGCGCGAGACACACTGCTCGTGCCCTAGTACGACTAACGGCTACTTCACGTCTCGCCGCG
         948           960           972           984           996          1008
```

TABLE 1-continued

```
                                                                          PvuI
                                                                          ClaI
GGGGCGTACCGGCACGCTGTTTGCGATGGAGCAGATGGGCGTTGCGCCGGATCTTACCACCTTTGCGAAATC
CCCCGCATGGCCGTGCGACAAACGCTACCTCGTCTACCCGCAACGCGGCCTAGAATGGTGGAAACGCTTTAG
     1020        1032        1044        1056        1068        1080
```

```
PvuI
ClaI                                         BssHII
GATCGCGGGCGGCTTCCCGCTGGCGGGCGTCACCGGGCGCGCGGAAGTAATGGATGCCGTCGCTCCAGGCGG
CTAGCGCCCGCCGAAGGGCGACCGCCCGCAGTGGCCCGCGCGCCTTCATTACCTACGGCAGCGAGGTCCGCC
     1092        1104        1116        1128        1140        1152
```

```
TCTGGGCGGCACCTATGCGGGTAACCCGATTGCCTGCGTGGCTGCGCTGGAAGTGTTGAAGGTGTTTGAGCA
AGACCCGCCGTGGATACGCCCATTGGGCTAACGGACGCACCGACGCGACCTTCACAACTTCCACAAACTCGT
     1164        1176        1188        1200        1212        1224
```

```
GGAAAATCTGCTGCAAAAAGCCAACGATCTGGGGCAGAAGTTGAAAGACGGATTGCTGGCGATAGCCGAAAA
CCTTTTAGACGACGTTTTTCGGTTGCTAGACCCCGTCTTCAACTTTCTGCCTAACGACCGCTATCGGCTTTT
     1236        1248        1260        1272        1284        1296
```

```
ACACCCGGAGATCGGCGACGTACGCGGGCTGGGGGCGATGATCGCCATTGAGCTGTTTGAAGACGGCGATCA
TGTGGGCCTCTAGCCGCTGCATGCGCCCGACCCCCGCTACTAGCGGTAACTCGACAAACTTCTGCCGCTAGT
     1308        1320        1332        1344        1356        1368
```

```
                                                                    StuI
CAACAAGCCGGACGCCAAACTCACCGCCGAGATCGTGGCTCGCGCCCGCGATAAAGGCCTGATTCTTCTCTC
GTTGTTCGGCCTGCGGTTTGAGTGGCGGCTCTAGCACCGAGCGCGGGCGCTATTTCCGGACTAAGAAGAGAG
     1380        1392        1404        1416        1428        1440
```

```
                          FspI
CTGCGGCCCGTATTACAACGTGCTGCGCATCCTTGTACCGCTCACCATTGAAGACGCTCAGATCCGTCAGGG
GACGCCGGGCATAATGTTGCACGACGCGTAGGAACATGGCGAGTGGTAACTTCTGCGAGTCTAGGCAGTCCC
     1452        1464        1476        1488        1500        1512
```

```
TCTGGAGATCATCAGCCAGTGTTTTGATGAGGCGAAGCAGTAGCGCCGCTCCTATGCCGGAGAGCACTGCGC
AGACCTCTAGTAGTCGGTCACAAAACTACTCCGCTTCGTCATCGCGGCGAGGATACGGCCTCTCGTGACGCG
     1524        1536        1548        1560        1572        1584
```

```
                BamHI
GTCTTGTCCGGCCTACGGGGATCC
CAGAACAGGCCGGATGCCCCTAGG
     1596        1608
```

TABLE 4

(I)  5' CGAAGATTACTTAGAAATCAAATATATGTGCATCGGTCTTTAACTGGAGAATGCGA ATG AAC AGC AAT... 3'
                                                                  Met Asn Ser Asn...

(II)                      5' ATATATGTGCATCGGTCTTTAACTGGAGAATGCGA ATG AAC AGC AAT... 3'
                                                                  Met Asn Ser Asn...

(III)                                       5' NcoI                              3'
                                             CCATGGA ATG AAC AGC AAT...
                                                     Met Asn Ser Asn...

(IV)                                        5' NcoI                              3'
                                             CC ATG GAC AGC AAT...
                                                Met Asp Ser Asn...

TABLE 5

L-PPT-specific transaminase activities in transformants of *E. coli* JM103 with various lac expression plasmids.

| Plasmid: | Medium: | Spec. transaminase activity [nmol of L-PPT/min/mg of cells]: |
|---|---|---|
| pTrans4 | LB | 22.8 |
|  | LB + 0.5% gluc. | 0.6 |
| pTrans5 | LB | 25.7 |
|  | LB + 0.5% gluc. | 1.2 |
| pTrans6 | LB | 24.5 |
|  | LB + 0.5% gluc. | 1.2 |
| pTrans7 | LB | 24.9 |
|  | LB + 0.5% gluc. | 0.9 |
| pTrans3 | LB | 9.7 |
|  | LB + 0.5% gluc. | 0.9 |
| pUC12 | LB | 0.9 |
|  | LB + 0.5% gluc. | 0.1 |

TABLE 6

L-PPT-specific transaminase activities in transformants of *E. coli* JM103 with various tac expression plasmids.

| Plasmid: | Medium: | Spec. transaminase activity [nmol of L-PPT/min/mg of cells]: |
|---|---|---|
| pTrans8 | LB | 11.4 |
|  | LB + 1 mM IPTG | 20.5 |
|  | LB + 0.5% gluc. | 2.6 |
|  | LB + 0.5% gluc. + 1 mM IPTG | 12.9 |
| pTrans9 | LB | 9.6 |
|  | LB + Mm IPTG | 21.7 |
|  | LB + 0.5% gluc. | 3.9 |
|  | LB + 0.5% gluc. + 1 mM IPTG | 11.3 |
| pTrans10 | LB | 2.3 |
|  | LB + 1 Mm IPTG | 16.6 |
|  | LB + 0.5% gluc. | 0.7 |
|  | LB + 0.5% gluc. + 1 Mm IPTG | 4.5 |
| pTrans11 | LB | 5.9 |
|  | LB + 1 mM IPTG | 20.9 |
|  | LB + 0.5% gluc. | 2.2 |
|  | LB + 0.5% gluc. + 1 mM IPTG | 22.1 |
| Ptrans3 | LB | 10.2 |
|  | LB + 1 mM IPTG | 10.7 |
|  | LB + 0.5% gluc. | 0.3 |
|  | LB + 0.5% gluc. + 1 mM IPTG | 0.4 |
| pJF 118u | LB | 1.0 |
|  | LB + 1 mM IPTG | 0.9 |
|  | LB + 0.5% gluc. | 0.2 |
|  | LB + 0.5% gluc. + 1 mM IPTG | 0.3 |

We claim:

1. A process for the stereoselective production of L-2-amino-4-methylphosphinobutyric acid from (3-carboxy-3-oxopropyl)-methylphosphinic acid by transamination with a microorganism comprising:
   (a) incubating a microorganism transformed with a plasmid that contains a gene for a transaminase specific for L-2-amino-4-methylphosphinobutyric acid, located on a 3.8 kb BamHI/SalI fragment obtainable from the genome of *E. coli* K12; and
   (b) bringing about production of said transaminase.

2. A process for the stereoselective production of L-2-amino-4-methylphosphinobutyric acid from (3-carboxy-3-oxopropyl)-methylphosphinic acid by transamination with a microorganism comprising:
   (a) incubating a microorganism transformed with a plasmid that contains a gene as claimed in claim 1, having the restriction map shown in FIG. 1; and
   (b) bringing about production of said transaminase.

3. A process for the stereoselective production of L-2-amino-4-methylphosphinobutyric acid from (3-carboxy-3-oxopropyl)-methylphosphinic acid by transamination with a microorganism comprising:
   (a) incubating a microorganism transformed with a plasmid that contains a gene for a transaminase specific for L-2-amino-4-methylphosphinobutyric acid, located on a 1.6 kb DraI/BamHI fragment from the genome of *E. coli* DH1, having the DNA sequence shown in FIG. 6; and
   (b) bringing about production of said transaminase.

4. A transaminase which is specific for L-2-amino-4-methylphosphinobutyric acid and has the amino acid sequence shown in FIG. 6.

5. A process for the stereoselective production of L-2-amino-4-methylphosphinobutyric acid from (3-carboxy-3-oxopropyl)-methylphosphinic acid by transamination with a microorganism, comprising:

(a) incubating a microorganism transformed with a plasmid containing a gene coding for an enzyme having the amino acid sequence shown in FIG. 6, wherein said enzyme is specific for L-2-amino-4-methylphosphinobutyric acid;

(b) producing said transaminase; and (c) using said transaminase for the stereoselective production of L-2-amino-4-methylphosphinobutyric acid from (3-carboxy-3-oxopropyl)-methylphosphinic acid.

* * * * *